US00PP09732P

United States Patent [19]

Dümmen

[11] Patent Number: Plant 9,732

[45] Date of Patent: Dec. 3, 1996

[54] GERANIUM PLANT NAMED 'HWD OPAL'

[75] Inventor: Günter Dümmen, Rheinberg-Eversael, Germany

[73] Assignee: Dummen Jungpflanzenkulturen, Rheinberg-Eversael, Germany

[21] Appl. No.: 522,002

[22] Filed: Aug. 31, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Proprietary Rights International

[57] ABSTRACT

A new and distinct cultivar of Geranium plant named HWD Opal, characterized by its semi-double red purple flowers; large umbels; numerous flowers per umbel; large flowers; short peduncles; zonation pattern on medium green foliage; and compact plant habit.

1 Drawing Sheet

The present invention relates to a new and distinct cultivar of Geranium plant, botanically known as *Pelargonium× hortorum,* known as the variety Dueopal, and hereinafter referred to by the cultivar name HWD Opal.

The new cultivar is a product of a planned breeding program conducted by the inventor in Rheinberg, Germany. The objective of the breeding program was to develop a new early-flowering semi-double geranium with red purple-colored flowers.

The new cultivar originated from a cross made by the inventor of the nonpatented cultivar Duecon as the male or pollen parent with the proprietary selection 90-20-2 as the female or seed parent.

The cultivar HWD Opal was discovered and selected by the inventor as a flowering plant within the progeny of the stated cross in a controlled environment in Rheinberg, Germany. Asexual reproduction of the new cultivar by terminal cuttings taken at Rheinberg, Germany, has shown that the unique features of this new Geranium are stabilized and reproduced true to type in successive generations of asexual reproduction.

The following traits have been repeatedly observed and are determined to be the unique characteristics of HWD Opal. These characteristics in combination distinguish HWD Opal as a new and distinct cultivar:

1. Semi-double red purple flowers.
2. Large umbels.
3. Numerous flowers per umbel.
4. Large flowers.
5. Short peduncles.
6. Zonation pattern on medium green foliage.
7. Compact plant habit.

In comparison to the parent cultivar Duecon, Plants of the new Geranium are more compact and have darker foliage and petal color. In comparison to the parent selection 90-20-2, plants of the new Geranium have lighter foliage and petal color.

The new Geranium is similar in petal color to the patented cultivars Fisbra (U.S. Plant Pat. No. 8,458), Designer Hot Pink (U.S. Plant Pat. No. 8,525) and Fisbluri (U.S. Plant Pat. No. 8,712). In comparison to the cultivar Fisbra, plants of the new Geranium have larger flowers and lighter green foliage color with a zonation pattern. Compared to plants of the cultivar Designer Hot Pink, plants of the new Geranium have larger umbels, shorter peduncles, larger flowers, and a zonation pattern on the foliage. Compared to plants of the cultivar Fisbluri, plants of the new Geranium have shorter peduncles, larger flowers and lighter foliage color.

The accompanying colored photograph illustrates the overall appearance of the new cultivar, showing the colors as true as it is reasonably possible to obtain in colored reproductions of this type. The photograph comprises a top perspective view of a typical potted plant of HWD Opal with one plant in a 10-cm container.

The cultivar HWD Opal has not been observed under all possible environmental conditions. The phenotype may vary somewhat with variations in environment such as temperature and light intensity, without, however, any variance in genotype. The following observations, measurements and comparisons describe plants grown in Rheinberg, Germany, under commercial practice in a glass-covered greenhouse with day temperatures of 24° C. and night temperatures of 18° to 20° C. and light levels of 45,000 to 60,000 lux. Plants were grown in 10-cm pots with one plant per pot.

In the following description, color references are made to the Royal Horticultural Society Colour Chart except where general terms of ordinary dictionary significance are used.

Classification:

*Botanical.*—*Pelargonium×hortorum.*

*Commercial:* Zonal Geranium.

*Cultivar:* 'HWD Opal'.

Parentage:

*Male parent.*—Cultivar Duecon.

*Female parent.*—Proprietary selection 90-20-2.

Propagation:

*Type cutting.*—Terminal cuttings.

*Time to initiate roots.*—Summer: 27° C., 21 days; winter: 20° C., 28 days.

Plant description:

*General appearance.*—Rounded; compact plant size; upright; freely branching.

*Foliage description.*—Arrangement: Generally alternate. Shape: Orbicular with rounded tip and cordate base. Size: Length: 6.5 to 7.5 cm. Width: 8.5 to 10 cm. Texture: Velvety; pubescent on upper and under surfaces. Margin: Crenate. Color: Young foliage, upper surface: 147B. Young foliage, under surface: 137C. Mature foliage, upper surface: 147B. Mature foliage, under surface: 137B. Zone, upper surface: 147A. Zone, under surface: None. Veins, upper surface: 144B. Veins, under surface: 144B. Petiole: 144A. Zonation: Width of zone: 2 cm. Location of zone: 1 to 1.5 cm from margin and 2 cm from petiole. Venation pattern: Palmate. Petiole: Length: 6.5 to 7.5 cm. Diameter: 1.5 to 2 mm.

*Stem description.*—Internode length: 0.5 to 1 cm. Stem color: 144A. Lateral branch number: 5. Lateral branch length: 5 to 6 cm.

Flowering description:

*Flowering habit.*—Freely flowering. Flowers arranged in umbels.

*Natural flowering season.*—Year-round.

*Flowers borne.*—Flower buds develop in apical leaf axils. Umbels are displayed above the foliage.

*Quantity of inflorescences.*—Very floriferous; usually 6 open umbels and at least 2 developing umbels per plant at one time.

*Umbels.*—Form: Rounded. Diameter: 12 to 13 cm. Depth (height): 8 to 10 cm.

*Flowers.*—Form: Semi-double. Shape: Rounded. Quantity of flowers per umbel: 25 to 40. Diameter: 5 to 6 cm. Depth (height): 2.5 to 3 cm.

*Petals.*—Shape: Obovate with rounded tip. Arrangement: Rosette, overlapping. Quantity: 6 to 7. Aspect: Flat. Size: Length: 3 to 3.2 cm. Width: 2.5 to 2.9 cm. Texture: Satiny, smooth. Margin: Entire. Color: When opening, upper surface: 57C. When opening, under surface: 55C. Upper surface: 57C. Under surface: 66D with 66B venous areas. Fading to, upper surface: Base of petals fade to 155D with venous areas, 66B. Fading to, under surface: Base of petals fade to 155D with venous areas, 66B.

*Petaloids.*—Shape: Irregular, generally obovate with rounded or clefted tip. Arrangement: Rosette, overlapping. Quantity: 4 to 5. Size: length: 2.5 cm. Width: 1.5 cm. Texture: Satiny, smooth. Margin: Generally entire. Color: When opening, upper surface: 57C. When opening, under surface: 55C. Upper surface: 57C. Under surface: 66D with 66B venous areas. Fading to, upper surface: Base of petals fade to 155D with venous areas, 66B. Fading to, under surface: Base of petals fade to 155D with venous areas, 66B.

*Peduncle (umbel stem).*—Angle: Erect, rigid. Length: 13 to 15 cm. Pubescence: Very fine. Color: 144A.

*Pedicel (individual flower stem).*—Angle: Erect, rigid. Length: 3.5 to 3.8 cm. Pubescence: Very fine. Color: 59B with hint of 144A.

*Flower bud.*—Shape: Ovoid. Length: 1.5 cm. Diameter: 8 mm. Color: 62A with margin of 57A.

*Sepals.*—Arrangement: Rosette. Quantity: 6. Size: Length: 1 cm. Width: 3 to 4 mm. Shape: Acuminate with apiculate tip. Texture: Velvety. Margin: Entire. Color: Upper surface: 60C at base fading to 144B at tip. Under surface: 60C at base fading to 144B at tip.

*Reproductive organs.*—Androecium: Stamen number: 13. Anther size: 2 mm. Anther color: 44A. Pollen color: 32B. Gynoecium: Pistil number: 1. Pistil length: 0.9 1 to 1 cm. Stigma shape: Decurrent. Stigma color: 58B. Style length: 3 mm. Style color: 58B.

*Ploidy level.*—Tetraploid.

Disease resistance: No fungal, bacterial nor viral problems observed.

Seed development: Seed production is very rarely observed.

It is claimed:

1. A new and distinct cultivar of Geranium plant named HWD Opal, as illustrated and described.

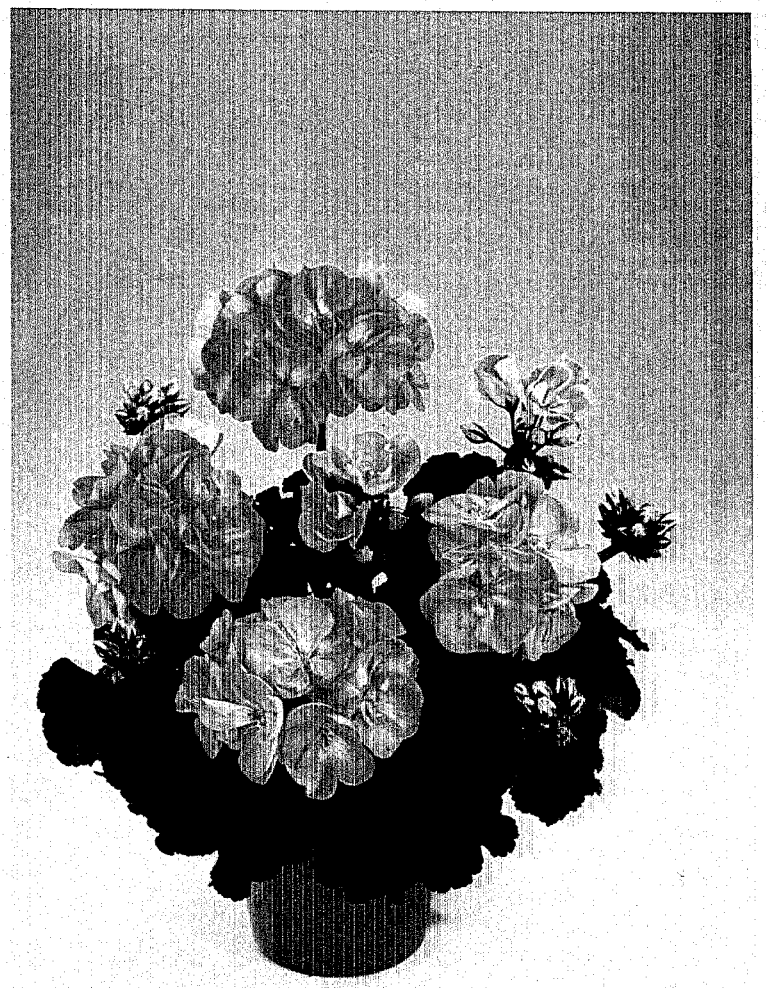

* * * * *